United States Patent [19]

Rickards

[11] 4,228,803

[45] Oct. 21, 1980

[54] PHYSIOLOGICALLY ADAPTIVE CARDIAC PACEMAKER

[75] Inventor: Anthony F. Rickards, London, England

[73] Assignee: Credit du Nord International N.V., Willemstad, Netherlands Antilles

[21] Appl. No.: 949,044

[22] Filed: Oct. 6, 1978

[30] Foreign Application Priority Data

Jun. 23, 1978 [GB] United Kingdom ............... 27693/78

[51] Int. Cl.³ ............................................. A61N 1/30
[52] U.S. Cl. ............................................. 128/419 PG
[58] Field of Search .................. 128/419 PG, 419 PT, 128/703, 710

[56] References Cited

U.S. PATENT DOCUMENTS

| | | | |
|---|---|---|---|
| 3,593,705 | 7/1971 | Thomas et al. ........................ | 128/703 |
| 3,593,718 | 7/1967 | Krasner et al. ............... | 128/419 PG |
| 3,658,055 | 4/1972 | Abe et al. ............................... | 128/703 |
| 3,857,399 | 12/1974 | Zacouto ......................... | 128/419 PG |
| 3,942,534 | 3/1976 | Allen et al. ..................... | 128/419 PG |
| 4,088,139 | 5/1978 | Auerbach ....................... | 128/419 PT |
| 4,091,817 | 5/1978 | Thaler ............................ | 128/419 PG |
| 4,096,865 | 6/1978 | Auerbach et al. .............. | 128/419 PT |

Primary Examiner—William E. Kamm
Attorney, Agent, or Firm—Woodcock, Washburn, Kurtz, Mackiewicz & Norris

[57] ABSTRACT

A cardiac pacemaker is disclosed having means for automatically adjusting the rate of operation to correspond to physiological changes. Circuitry is provided for detecting the presence or absence of an evoked T wave following a delivered stimulus pulse, and for measuring the time interval between the stimulus pulse and the following T wave. The escape interval of the pacemaker pulse generator is varied in accordance with the detected stimulus-T interval and in the same direction, so as to vary the pacing rate in accordance with variations in such interval. Since this interval in turn corresponds to physiological changes, the pacemaker is adapted to automatically follow the patient's physiological changes.

37 Claims, 3 Drawing Figures

PHYSIOLOGICALLY ADAPTIVE CARDIAC PACEMAKER

BACKGROUND OF THE INVENTION

This invention relates to a cardiac pacemaker for delivering electrical stimuli to the heart for the purpose of stimulating the heart to react electrically and thus contract mechanically. A pacemaker consists of an electronic generator connected through an electrode to the ventricular myocardium of the heart; the electrode may be unipolar or bipolar.

Although fixed rate generators are known which provide electrical stimuli to the heart at fixed and preset intervals, the present invention is concerned with a pacemaker having a demand generator, which is sensitive to the electrical activity of the heart. The demand generator includes a timing circuit which, unless disabled, causes a stimulus to be delivered at the end of an escape interval. If there is no intrinsic, or naturally occurring, heart activity, the ventricles are electrically inactive and the demand generator acts as a fixed rate generator and delivers pacing stimuli to the heart. If, however, the generator senses an intrinsic heart activity during an escape interval, then the timing circuit is restarted without causing a stimulus, while, if no ventricular activity is sensed during the escape interval, a stimulus is delivered by the generator at the end of that interval and the timing circuit restarted. The initial escape interval and the subsequent pacing interval between consecutive stimuli may be identical, or different. Thus, a demand generator delivers stimuli designed to depolarise the heart only if the natural ventricular rate falls below a preset value corresponding to the escape interval.

With a healthy heart, the natural rate of ventricular activity responds to nervous and humoral stimuli; in the normal individual, exercise results in an increasing heart rate, which is accomplished by nervous and humoral stimuli increasing the rate at which the natural pacemaker of the heart—the sinus node—depolarises. A pacemaker having a demand generator as described above is incapable of responding to physiological conditions which, in the normal individual, would cause an increase in heart rate. While there have bee proposals to cause the pacemaker to react to the physiological conditions of the individual, e.g. atrial activity, tissue pH or respiratory rate, all those proposals have required detectors which are additional to the pacemaker and which sense the required condition.

The present invention is based on my realisation that the period of ventricular repolarisation—the interval between the onset of ventricular depolarisation (the QRS complex) and repolarisation (the T wave)—decreases with increase in heart rate, due to the action of hormones released into the blood stream with cardiac effects. In the present invention, the interval between a pacing stimulus delivered by a pacemaker generator and the evoked repolarisation sets the escape interval of the generator for the subsequent stimulus, and thus controls the heart rate.

SUMMARY OF THE INVENTION

According to the present invention, a cardiac pacemaker comprises a stimulus generator arranged to deliver an electrical cardiac stimulus in the absence of a detected intrinsic heart activity occurring within a predetermined, but adjustable, escape interval, and a circuit for detecting the period between a delivered stimulus and a detected ventricular repolarisation (T wave) resulting therefrom, and for varying the predetermined escape interval of the generator in accordance with the detected period. The escape interval is varied in the same direction as the detected period, but not necessarily proportionally.

The invention has the merit that the pacemaker can vary the induced heart rate in accordance with the body requirements using signals sensed from the pacemaker itself, and without the use of special detectors for sensing conditions elsewhere in the body.

In order that the detecting circuit shall be ineffective when a normal intrinsic heart activity occurs, there is preferably provided a circuit which responds only to pacing stimuli and which renders operative the detecting circuit.

BRIEF DESCRIPTION OF THE DRAWINGS

The invention will be more readily understood by way of example from the following description of a cardiac pacemaker in accordance therewith, reference being made to the accompanying drawings, in which.

DESCRIPTION OF THE PREFERRED EMBODIMENTS

Figure 1:
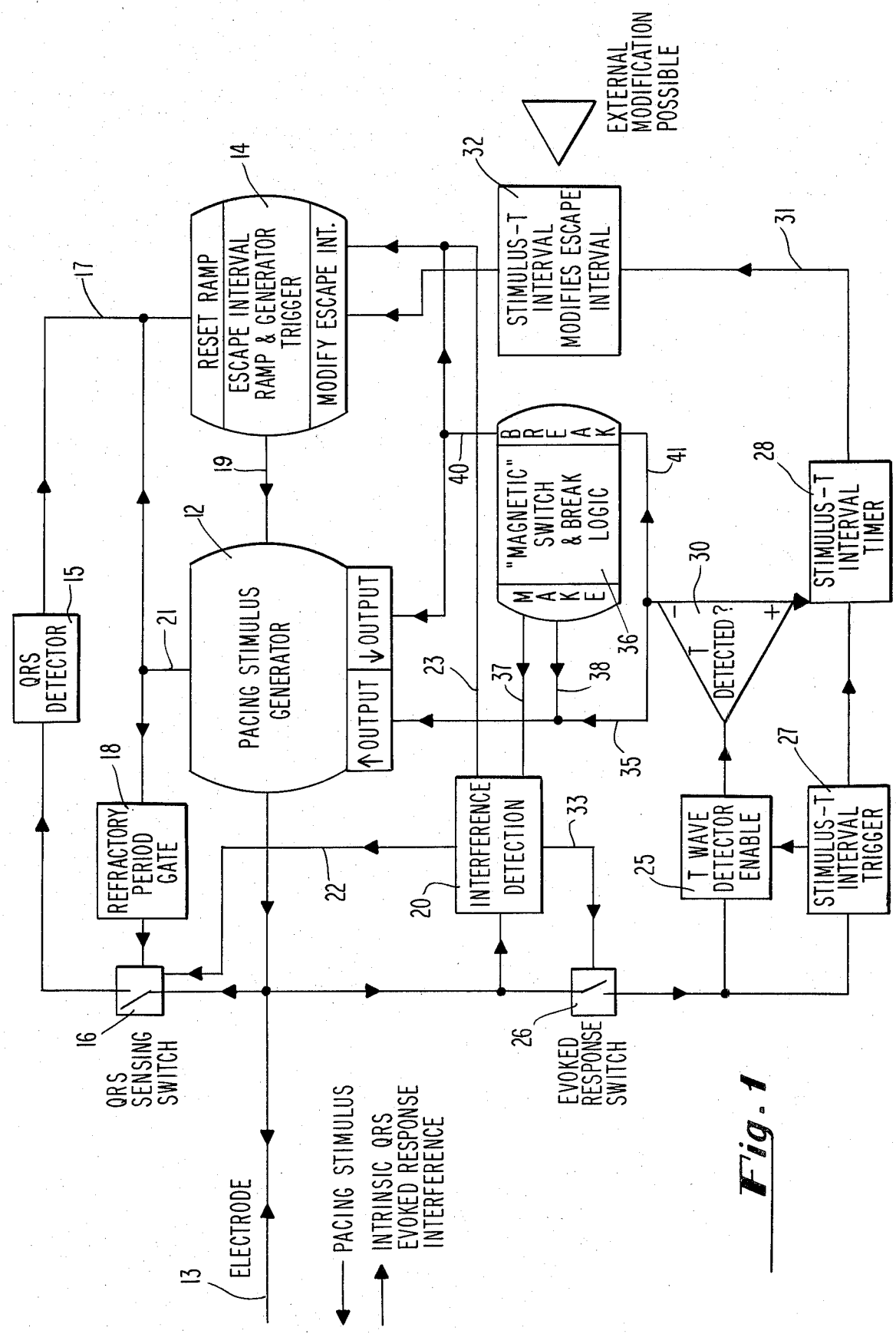
FIG. 1 is a block schematic circuit diagram of the pacemaker.

The pacemaker circuit shown in FIG. 1 consists of a generator circuit 12, which emits a stimulus pulse on the electrode 13, when triggered by a trigger circuit 14. The trigger circuit 14 generates a ramp voltage with an adjustable rate of rise and, when the voltage exceeds a fixed value emits a trigger pulse on line 19 to trigger the generator circuit 12.

QRS detector 15 is connected through a switch 16 to the electrode and is capable of detecting the spontaneous QRS complex of an intrinsic heart activity. When the complex is detected, a signal is passed on line 17 to reset the trigger circuit 14. The switch 16, which can be an electronic gate, is controlled, firstly, by a refractory period gate 18 and, secondly, by an interference detector 20. When the generator circuit 12 emits a stimulus to the electrode 13, a signal is simultaneously emitted on line 21 to reset the trigger circuit 14 and to operate gate 18 which opens switch 16 for a predetermined period which is greater than the interval between the delivery of a stimulus by generator circuit 12 and the QRS complex of the evoked response. The detector 20 detects external electromagnetic interference and, on the occurrence of such a detected interference picked up the eletrode 13, opens the switch 16, thereby disabling the detector 15. Simultaneously, detector 20 passes on line 23 a signal to control the trigger 14.

The circuit so far described is already known and operates as follows: the trigger circuit 14 is set to give an escape interval corresponding to the lowest desired pacing rate. The escape interval is the inverval needed for the ramp voltage to reach the fixed value after being reset. During intrinsic heart activity, the generator circuit 12 is quiescent, because the arrival of each QRS complex is detected by detector 15 and the trigger circuit 14 is reset before the ramp voltage reaches the fixed value and causes the generator circuit 12 to be triggered. If an intrinsic QRS complex is not detected within the escape interval, the generator circuit 12 is triggered and emits a stimulus to the electrode 13, and simultaneously resets the trigger 14 to initiate the next escape interval, and opens switch 16 for a period sufficiently long to prevent the detector 15 receiving the evoked response of the stimulus.

If an intrinsic QRS complex arrives before the end of the next escape interval, the trigger circuit 14 is reset, so that no stimulus is generated by the generating circuit 12. If, however, no QRS complex is detected within that escape interval, the generator 12 is triggered and produces a stimulus, as before.

If the interference detector 20 detects the presence of external electromagnetic interference, switch 16 is opened to disable detector 15 for so long as the interference subsists. Simultaneously, the detector 20 causes the rate of the ramp voltage generated by the trigger circuit 14 to be modified, in order to decrease the escape interval to a predetermined rate (say 90 per minute) which may or may not be faster than that corresponding to the normal escape interval of the circuit. The consequence is that, so long as the interference continues, pacing stimuli are emitted to electrode 13 at a fixed rate, regardless of intrinsic heart activity.

In order that the pacemaker should react to physiological changes, the pacemaker circuit as described above is modified as follows: a T wave detector 25 is connected to the electrode 13 through an evoked response switch 26 and is designed to detect ventricular repolarisation. Detector 25 is normally disabled, but can be enabled by a trigger circuit 27, which is also connected to switch 26 and which can be energised only by a stimulus emitted by generating circuit 12, and not by an intrinsic QRS complex. When energised, trigger 27 emits after a short predetermined interval an enabling signal to T wave detector 25. The stimulus pulse is also applied by trigger circuit 27 to a timing circuit 28, but without a delay; timing circuit 28 is then set in operation. When detector 25 detects a T wave, it passes a pulse to logic circuit 30, which detects the presence or absence of a T wave. If a T wave is detected, the pulse is applied to timing circuit 28 which ceases its timing operation and emits on line 31 a signal representing the measured time interval which is the interval between the receipt of the stimulus and the receipt of the T wave. The signal is applied to a modifying circuit 32 which modifies the escape interval of trigger circuit 14, by altering the rate at which the ramp voltage increases. If the stimulus-T wave interval, as measured by timing circuit 28 decreases, the escape interval is also decreased, but not necessarily proportionally.

If, then, the physiological conditions of the patient alters to require a faster rate of pacing, the physiological change is detected by a reduction in the stimulus-T wave interval. The resulting decrease in the escape interval of trigger circuit 14 causes the generating circuit 12 to deliver stimuli at a higher rate. If an intrinsic QRS activity is at any time detected by detector 15, the trigger circuit 14 is reset as before, and T wave detector 25 will not be enabled, since trigger circuit 27 is operated only by stimuli, with the result that the escape interval modification circuit is inoperative. If external electromagnetic interference is present, the interference detector 20 opens the evoked response switch 26 through line 33 and the pacemaker returns to the fixed rate pacing mode described above in relation to interference detection.

Figure 2:
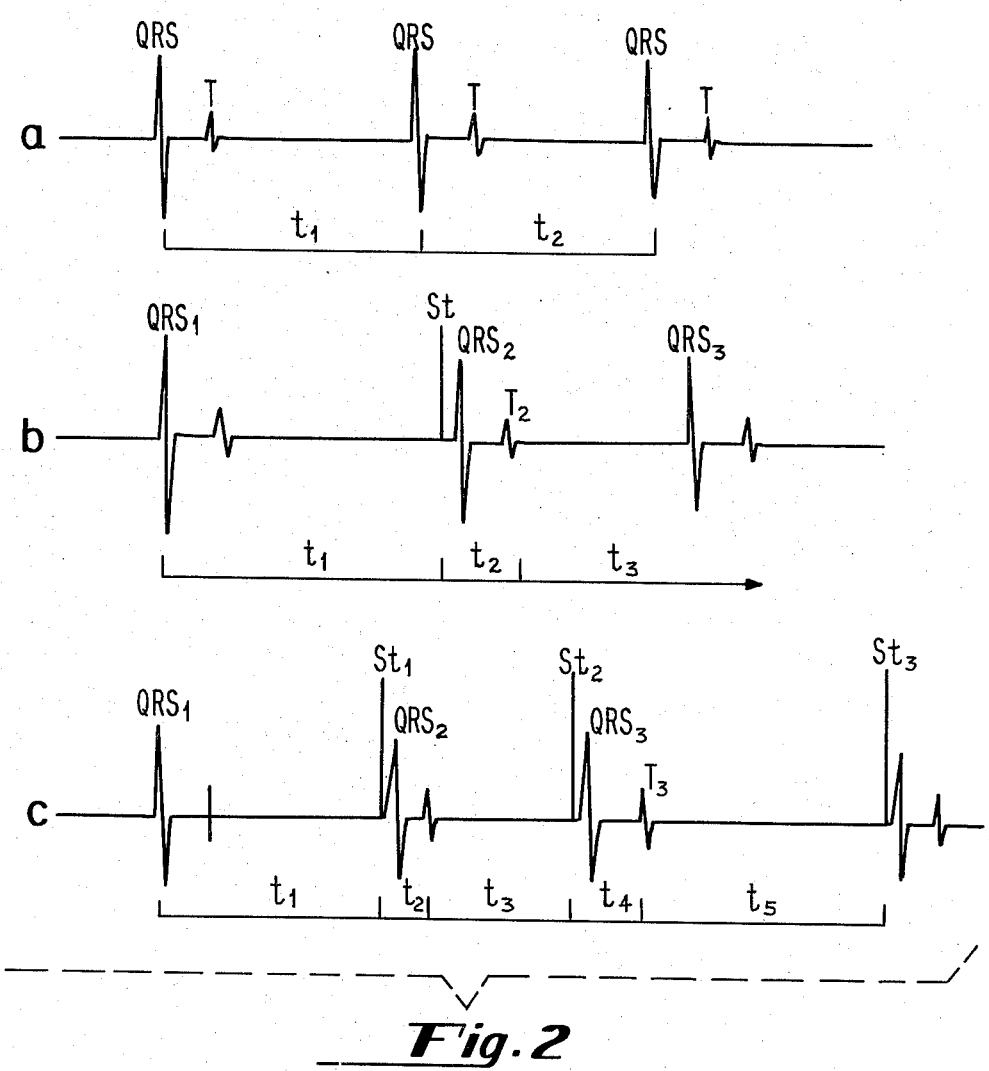
FIG. 2, lines a, b and c are traces explaining the operation of one part of the pacemaker's circuit.

The operation of the circuit just described for varying the escape interval is illustrated in FIG. 2. FIG. 2, line a represents the condition where intrinsic QRST compleses are detected. Provided that the times $t_1$ and $t_2$ between successive QRS complexes detected by detector 15 are less than the escape interval of the trigger circuit 14, there is no pacing stimulus generated. In FIG. 2, line b, no subsequent QRS complex is detected by detector 15 within the escape interval of the generator and, therefore, a stimulus St is delivered to the electrode 13 and therefore to the heart, producing an evoked response—$QRS_2$. The time interval $t_2$ from the stimulus St to the T wave of the evoked response is measured by timing circuit 28 and the escape interval $t_3$ of the trigger circuit 14 is modified appropriately. A naturally occurring complex $QRS_3$ occurring before the end of the new escape interval $t_3$ inhibits the pacing generator 12.

FIG. 2, line c demonstrates the situation where a naturally occurring QRS complex is not detected by detector 15 in the new escape interval $t_3$. In that case, a second stimulus $St_2$ is generated and, as before, the interval $t_4$ between stimulus $St_2$ and the T wave—$T_3$ of the evoked response is measured and sets the escape interval for the next period. FIG. 2, line c shows that $t_4$ is considerably longer than $t_2$, and therefore the new escape interval $t_5$ is again increased. The figure also shows the absence of a detected QRS complex in the new escape interval $t_5$ and therefore the production of a further stimulus $St_3$.

The voltage level of the stimulus generated by generating circuit 12 must of course be greater than the threshold-the value of that voltage below which cardiac electric activity or depolarisation does not consistently occur in response to the pacing stimuli. On the other hand, if the voltage level is too far above the threshold, wastage of battery energy occurs, requiring early battery replacement. The circuit of FIG. 1 includes circuit elements designed to maintained the stimulus energy level (particularly the stimulus voltage) voltage at a minimum level, but above the threshold.

Reverting to the logic circuit 30, the absence of a T wave following a stimulus is detected by circuits 25, 27 and 30 to cause a signal to be applied on line 35 to the stimulus generating circuit 12 and to increase the stimulus output level by one step. Thus, if the voltage level is initially at 25% of the maximum level, the generating circuit 12 is increased in successive cycles to 50%, 75% and 100% of the maximum, provided that no evoked response T wave is produced in those cycles.

The circuit includes a magnetic switch 36, usually a reed switch, activated externally by the physician. When the switch is activated to the "make" condition, it causes through line 37 the interference detector 20 to be switched on, causing the generating circuit 12 to emit stimuli continuously at a fixed rate as described above. Also, the magnetic switch applies through lines 38 and 35 a signal to the generating circuit 12 to cause the output stimulus level to be increased, as described, to the maximum value. When the magnet is removed and the magnetic switch returns to the "break" condition a signal is applied on line 40 to the generating circuit 12, to cause that circuit to reduce the output level in a sequence of steps in successive cycles. Also when the magnetic switch 36 is in the "break" condition, interference detector 20 is deenergised, causing T wave detector 25 to be operative, and the trigger circuit 14 receives the signal on line 40 to maintain the escape interval at a rate which may or may not be higher than the basic escape interval of trigger 14. In this way, the output level of the generating circuit 12 is reduced in steps, as long as detector 25 detects a T wave. As soon as the T wave detector 25 fails to detect a T wave, showing that the stimulus level is below the threshold, the resulting signal from logic circuit 30 is applied on line 41 to prevent further reduction in the energy level, and on line 35 to increase the level again by one step. If the absence of T wave is not detected, reduction of the output level of generating circuit 12 stops at a predetermined minimum of, say 25% of the maximum.

Figure 3:
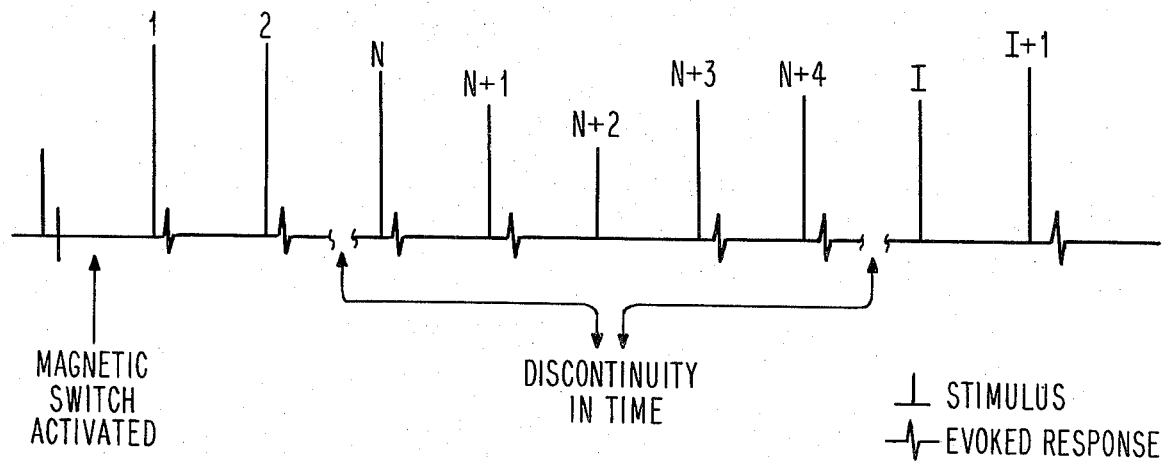
FIG. 3 explains the operation of a second part of the circuit.

The operation is illustrated diagrammatically in FIG. 3. The figure assumes that magnetic switch 36 is made at a time X. Generating circuit 12 is instructed to increase the output level to the maximum as shown at 1; that level is retained for test purposes for a further N−1 beats. The magnetic switch 36 is then brought to the "break" condition after the (N−1) beat, so that for the Nth beat the level is reduced to 75% of the maximum. Similarly, the level for the N+1 beat is 50% and that for the N+2 beat 25%. The 25% level of the N+2 beat is below the threshold and the resulting absence of a T wave is detected by logic circuit 30 to cause the level for the N+3 beat to be 50%, which produces an evoked response. The output level is thus retained at 50% for the N+4 beat and subsequent beats, unless of course the absence of a T wave is substantialy detected. If stimulus I does not produce an evoked response, that fact is detected by a logic circuit 30 and the output level of the stimulus generator is increased for stimulus I+1 to the 75% value.

It will therefore be seen that only the physician controlling the magnetic switch 36 can cause a reduction in stimulus output level, whereas the circuit automatically operates to increase the level if there should be no evoked response following a stimulus. In this way, the output level is maintained at that step immediately above the threshold and battery energy economy is achieved.

NOTES ACCOMPANYING DRAWINGS

FIG. 2.

A. Times $t_1$ and $t_2$ do not exceed the escape interval of the demand generator (which senses the QRS complexes) and is therefore inhibited from pacing.

b. Time $t_1$ is greater than the escape interval of the generator and a pacing stimulus (St) is delivered which evokes a QRST complex. The St to T wave interval ($t_2$) is measured and an escape interval $t_3$ is set. A naturally occurring QRST complex occurs before $t_3$ expires and inhibits the generator.

c. Time $t_1$ exceeds the escape interval of the generator and thus $St_1$ is delivered. The interval from stimulus to T wave is detected ($t_2$) and $t_3$—the generator escape interval set. Following stimulus 2 ($St_2$) the stimulus T interval is again sensed and the subsequent escape interval ($t_5$) set.

Thus the escape intervals following paced beats ($t_3$ and $t_5$) are a function of the stimulus-T intervals ($t_2$ and $t_4$) of the previous beats such that decreases in stimulus-T intervals produce decreases in escape intervals and thus increased rate.

FIG. 3.

Typical sequence following magnet switch activation:

Stimulus 1, 2 following magnet switch is at maximum output and remains there for testing purposes for N beats.

Stimulus N at say 75% output evokes a response.
Stimulus N+1 at say 50% output evokes a response.
Stimulus N+2 at say 25% output does not evoke a response.
Stimulus N+3 increases to 50% output—response evoked.

Typical "naturally" occurring sequence:
Stimulus I of say 50% does not evoke a response.
Stimulus I+1 increases to 75% output and evokes a response.

I claim:

1. A demand cardiac pacemaker having circuitry for carrying out demand pacer functions, adapted to be utilized in combination with an electrode for delivering stimulus signals to a patient's heart and for receiving from said patient's heart signals representative of heart activity, comprising:
    a. stimulus signal generator means for delivering stimulus signals, having modifiable means for setting its escape interval;
    b. T wave means for sensing a T wave of an evoked heart response following a delivered stimulus signal, and for determining the time relationship of said T wave relative to said delivered stimulus signal; and
    c. modifying means connected to said T wave means and said modifiable means for modifying said escape interval as a function of said time relationship.

2. The demand cardiac pacer as described in claim 1, wherein said T wave sensing means comprises stimulus detection means for detecting when a stimulus signal has been delivered and for enabling said T wave sensing means only upon detecting that a stimulus signal has been delivered.

3. The demand cardiac pacer as described in claim 2, wherein said stimulus detection means enables said T wave sensing means for only a limited time period following detection of a delivered stimulus signal.

4. The demand cardiac pacer as described in claim 3, wherein said stimulus detection means initiates said limited time period after a predetermined time delay following detection of a delivered stimulus signal.

5. The demand cardiac pacer as described in claim 1, comprising means for detecting the presence of electromagnetic interference and for operatively disconnecting said T wave means when said interference is detected to be present.

6. The demand cardiac pacer as described in claim 1, wherein said T wave means comprises a circuit for measuring the stimulus-T wave interval and for generating a signal representative of said measured interval.

7. The demand cardiac pacer as described in claim 6, wherein said modifying means has means for rendering it operative only following delivered stimulus signals, and said stimulus signal generator means has a predetermined normal escape interval at which it operates when not modified by said modifying means, such that the pacer escape interval is said normal escape interval following natural heartbeats.

8. The demand cardiac pacer as described in claim 7, wherein said modifying means is adapted for external modification of said function.

9. The demand cardiac pacer as described in claim 6, wherein said modifying means modifies said escape interval in the same direction as said measured interval.

10. The demand cardiac pacer as described in claim 1, comprising a common electrode connection means for connecting stimulus signals and detected heart signals to said T wave means.

11. In a demand pacer having a stimulus generator with an adjustable escape interval for delivering pacing stimuli, said pacer being adapted to receive signals representative of heart activity, the improvement consisting of means for setting said escape interval as a function of the time interval between a pacing stimulus delivered by said pacer and the evoked heart repolarization following such delivered stimulus.

12. The pacer as described in claim 11, comprising means for determining said time interval following each delivered stimulus, and means for setting said escape interval following each determined interval.

13. The pacer as described in claim 11, wherein said setting means sets said escape interval in the same direction as said time interval.

14. The pacer as described in claim 13, wherein said setting means function is non-proportional.

15. The pacer as described in claim 13, wherein said setting means function is proportional.

16. The pacer as described in claim 11, in combination with an electrode, which electrode is adapted to be placed in the ventricle for delivering pacing stimuli and for detecting QRS waves and T waves.

17. The pacer as described in claim 11, wherein said setting means has a circuit which detects said time interval after each delivered pacing stimulus, and a circuit which sets said escape interval subsequent to each delivered pacing stimulus as a predetermined function of the just detected time interval.

18. The pacer as described in claim 11, wherein said stimulus generator operates with a predetermined normal escape interval during said time interval, having circuit means for varying said escape interval following detection of the evoked repolarization.

19. The pacer as described in claim 18, wherein said stimulus generator includes circuitry for generating a ramp voltage with an adjustable rate of rise, and means for triggering generation of a pacing stimulus when said ramp voltage exceeds a fixed value.

20. The pacer as described in claim 11, comprising a QRS wave detecting circuit, wherein said setting means comprises a circuit for detecting a T wave representative of heart repolarization, said T wave detecting circuit and said QRS wave detecting circuit being connected to a common point wherein said heart activity signals are received.

21. A pacing system having a demand pacemaker with a stimulus generator for normally delivering stimulus signals at a normal rate and means for resetting said stimulus generator upon detection of a natural heartbeat, in combination with an electrode adapted to deliver stimulus signals to a heart and to provide signals representative of activity of said heart, said pacemaker being characterized by
 a. said stimulus generator having a circuit providing an adjustable escape interval, and
 b. comprising means for detecting the time relationships between delivered stimulus signals and the corresponding T waves following such delivered stimulus signals, and means for setting the escape interval of said stimulus generator as a function of said detected time relationships.

22. The system as described in claim 21, wherein said electrode is adapted to be positioned in the ventricle of said heart, said electrode having common means for delivering said stimulus signals to the heart and for sensing signals representative of heart T waves.

23. The system as described in claim 21, wherein said setting means has means for detecting T waves, and means for setting said escape interval following detection of a T wave, thereby controlling the timing of the next delivered stimulus signal.

24. The system as described in claim 23, wherein said setting means sets said escape interval for only the next stimulus signal following a detected T wave.

25. A demand cardiac pacer having a stimulus generator for generating stimulus pulses and demand logic circuitry for resetting said stimulus generator upon detection of a signal representing a natural heartbeat, further characterized by:
 means for sensing T wave signals;
 means for determining the time interval between a stimulus pulse and the following evoked T wave signal, and for generating a modifying signal corresponding to said time interval; and
 means for modifying the escape interval of said stimulus generator with said modifying signal.

26. A method of cardiac pacing of a patient wherein the rate of pacing is adapted to react to physiological changes, comprising:
 generating a first stimulus pulse and delivering said first stimulus pulse to said patient's heart, thereby evoking a heartbeat, said heartbeat including a QRS wave and a T wave;
 sensing said T wave of said evoked heartbeat;
 measuring the time interval between said T wave and a prior time reference point; and then
 delivering a next stimulus pulse after a second time interval which is a predetermined function of said determined time interval.

27. The method of pacing as described in claim 26, wherein said prior time reference point is the time of delivery of said first stimulus pulse.

28. A cardiac pacemaker adapted to react to physiological changes of the patient being paced by such pacemaker, comprising:
 stimulus generator means for generating stimuli for delivery to the patient's heart, said stimulus generator means having a variable escape interval;
 means for developing a signal corresponding to the QRS-T interval of a heart signal evoked by one of said stimuli; and
 means for varying said escape interval for the next subsequent stimulus as a function of said corresponding signal, thereby controlling the rate of said stimulus generator in accordance with said patient's changing QRS-T interval.

29. The cardiac pacemaker as described in claim 28, in combination with an electrode for delivering stimuli to said heart and providing signals representative of heart activity, said electrode being connected to said pacemaker so that said stimuli are delivered from and said signals are provided to a common point.

30. A method of cardiac pacing of a human patient, comprising:
 normally delivering stimulus signals to said patient;
 utilizing an electrode in contact with said patient's heart for delivering stimulus signals thereto;
 utilizing the same electrode for sensing the occurrence of natural QRS signals generated in said patient's heart, and inhibiting the delivery of the next said normally delivered stimulus signal following each sensed QRS signal;

utilizing the same electrode to sense the evoked T wave signal following delivery of a stimulus signal;

determining the time of delivering the next stimulus signal as a function of the timing of said sensed T wave signal; and delivering the next stimulus pulse at said determined time.

31. A cardiac pacemaker system comprising:

a stimulus generator circuit characterized by normally operating to generate successive pacing stimuli, said generator circuit having an escape interval circuit which controls the generator escape interval and thus the time rate of successive stimuli;

a circuit for measuring the stimulus-T wave interval for evoked heartbeats and for providing at its output a signal corresponding to said interval;

connecting circuitry connecting pacing stimuli to an output adapted for connection to a pacing electrode, and for connecting said output to said measuring circuit;

a pacing electrode connected to said output and adapted to deliver said pacing stimuli to a patient's heart and to deliver signals representative of the patient's heart activity to said circuit; and a circuit connected between said measuring circuit output and said escape interval circuit for modifying the operation of said escape interval circuit so as to control said escape interval.

32. A cardiac pacer having a stimulus generator with an adjustable escape interval for delivering pacing stimuli, said pacer having means for receiving signals representative of heart activity, wherein the improvement comprises means for detecting the T wave component of heart signals and means for setting said escape interval as a function of the time interval between the last delivered pacing stimulus and the detected T wave following said last delivered pacing stimulus.

33. A demand cardiac pacemaker having circuitry for carrying out demand pacer functions, adapted to be utilized in combination with an electrode for delivering stimulus signals to a patient's heart and for receiving from said patient's heart signals representative of heart activity, wherein the improvement comprises:

a. stimulus signal generator means for delivering stimulus signals, having modifiable means for setting its escape interval;

b. sensing means for sensing the T wave portion of the heartbeat signal of an evoked heart response following a delivered stimulus signal and deriving a signal therefrom, and for determining the time relationship of said derived signal relative to said delivered stimulus signal; and c. modifying means connected to said sensing means and said modifiable means for modifying said escape interval as a function of said time relationship.

34. The pacemaker as described in claim 33, wherein said modifying means function is non-proportional.

35. The pacemaker as described in claim 34, wherein said function is modifiable by an external source.

36. The pacemaker as described in claim 33, wherein said modifying means function is proportional.

37. The pacemaker as described in claim 36, wherein said function is modifiable by an external source.

* * * * *

UNITED STATES PATENT AND TRADEMARK OFFICE
CERTIFICATE OF CORRECTION

PATENT NO. : 4,228,803
DATED : October 21, 1980
INVENTOR(S) : Anthony F. Rickards It is certified that error appears in the above-identified patent and that said Letters Patent are hereby corrected as shown below:

Amend the title to read "PHYSIOLOGICALLY ADAPTIVE CARDIAC PACEMAKER AND METHOD OF CHANGING PACING RATE".

Column 2, line 43, change "intrinstic" to --intrinsic--.

Column 2, line 56, after "such" delete "a".

Column 2, line 63, change "inverval" to --interval--.

Column 5, line 30, change "substantialy" to --subsequently--.

Column 5, line 46, change "A." to --a.--.

Signed and Sealed this

Third Day of February 1981

[SEAL]

Attest:

RENE D. TEGTMEYER

Attesting Officer

Acting Commissioner of Patents and Trademarks